United States Patent [19]

Taylor

[11] Patent Number: 4,534,347
[45] Date of Patent: Aug. 13, 1985

[54] MICROWAVE COAGULATING SCALPEL

[75] Inventor: Leonard S. Taylor, Silver Spring, Md.

[73] Assignee: Research Corporation, New York, N.Y.

[21] Appl. No.: 483,219

[22] Filed: Apr. 8, 1983

[51] Int. Cl.$^3$ ............................................. A61B 17/36
[52] U.S. Cl. ............................ 128/303.1; 128/303.17
[58] Field of Search ........... 128/303.1, 303.13, 303.14, 128/303.15, 303.17, 305, 804

[56] References Cited

U.S. PATENT DOCUMENTS

| | | |
|---|---|---|
| Re. 29,088 | 12/1976 | Shaw . |
| 3,089,496 | 5/1963 | Degelman . |
| 3,786,814 | 1/1974 | Armao . |
| 3,826,263 | 7/1974 | Cage et al. . |
| 3,903,891 | 9/1975 | Brayshaw . |
| 3,987,795 | 10/1976 | Morrison . |
| 4,196,734 | 4/1980 | Harris . |
| 4,204,549 | 5/1980 | Paglione ........................ 128/804 X |
| 4,273,127 | 6/1981 | Auth et al. ........................ 128/303.1 |
| 4,312,364 | 1/1982 | Convert et al. ...................... 128/804 |
| 4,315,510 | 2/1982 | Kihn ................................. 128/303.1 |
| 4,318,409 | 3/1982 | Oosten . |
| 4,446,874 | 5/1984 | Vaguine ............................. 128/804 |
| 4,494,539 | 1/1985 | Zenitani et al. .................. 128/303.1 |

FOREIGN PATENT DOCUMENTS

| | | | |
|---|---|---|---|
| 2646029 | 4/1978 | Fed. Rep. of Germany ... | 128/303.1 |
| 1188490 | 4/1970 | United Kingdom ............... | 128/804 |

OTHER PUBLICATIONS

Article: "A New Operative Procedure of Heptatic Surgery Using a Microwave Tissue Coagulator" (Arch Jan Chir 48 (2), pp. 160-172, Mar. 1979) by: Katsuyoshi Tabuse.

*Primary Examiner*—Lee S. Cohen
*Attorney, Agent, or Firm*—Scully, Scott Murphy & Presser

[57] ABSTRACT

A microwave coagulating scalpel which simultaneously severs and coagulates highly vascular tissue is disclosed. The scalpel blade forms both a cutting edge and a microwave radiator loop, with the diameter of the loop related to the wave length of the microwave frequency, when the microwave energy is propogated in highly vascular tissue. A range of 100 $MH_z$ to 13,000 $MH_z$ is disclosed with preferential frequencies at 915 $MH_z$, 2450 $MH_z$ and 5800 $MH_z$. A means bolometer and threshold switch to de-energize the microwave source when the blade is removed from the highly vascular tissues also is disclosed.

40 Claims, 7 Drawing Figures

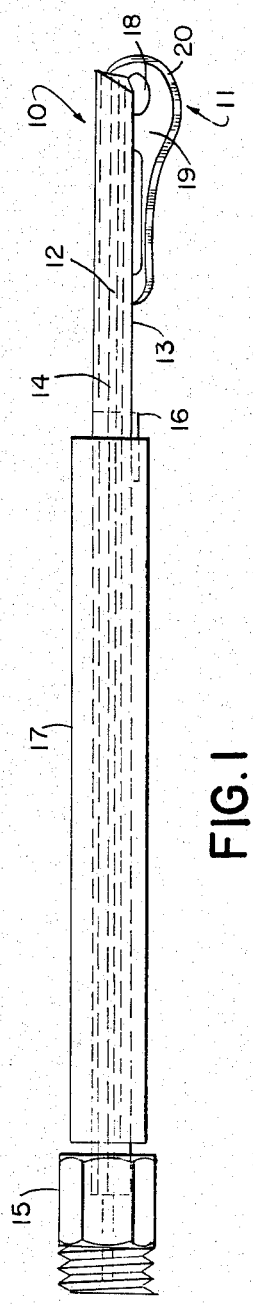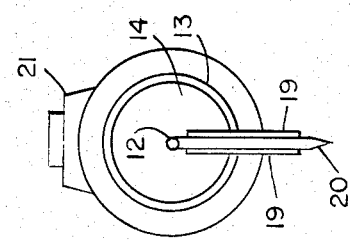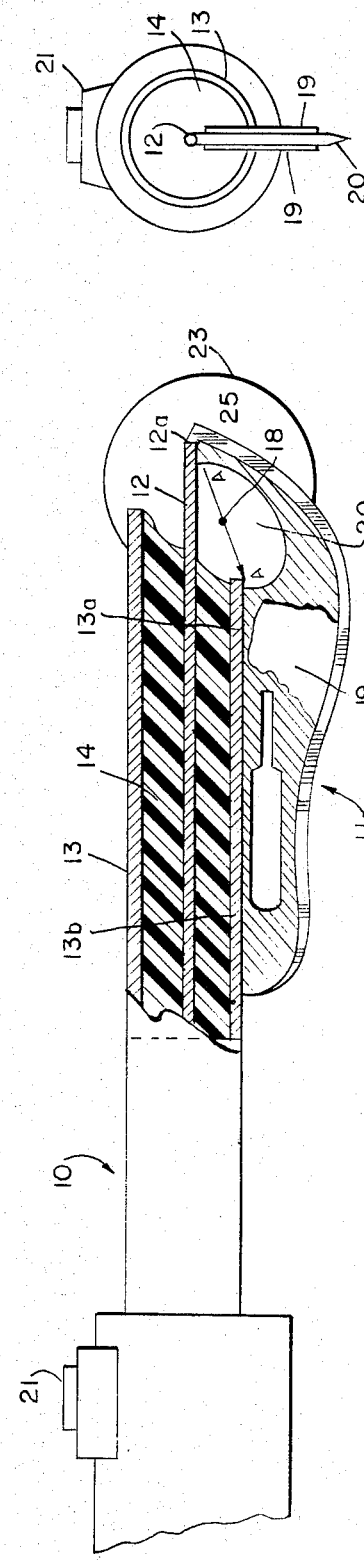

MICROWAVE COAGULATING SCALPEL

FIELD OF THE INVENTION

The present invention relates to a means and method of simultaneously severing and coagulating highly vascular tissue such as a spleen or liver. The need for splenic preservation is now universally accepted inasmuch as splenic functions include:
(1) hematopoiesis in utero;
(2) filtering of particulate matter;
(3) production of opsonins (tuftsins and properdin);
(4) production of IgM;
(5) regulation of T and B lymphocytes.

The present techniques used to sever and coagulate highly vascular tissue include the use of topical hemostatic agents, various mattress suture techniques, splenic artery ligation, and ligation of segmental branches of the splenic artery with segmental resection, all of which require a high degree of technical surgical skill. As a result, only 25 to 30 percent of traumatized spleens are currently being salvaged. The present invention, using a new microwave coagulating technique provides a safe and rapid means of splenic and hepatatic surgery. The microwave induced thermal field creates a coagulated crust which rapidly heals through the development of psuedocapsule. The device may have wide application in military medicine where physical trauma to the liver and spleen is a recurring problem.

DESCRIPTION OF THE PRIOR ART

The present surgical techniques employ the use of resistance heated scalpels, radio frequency scalpels, both unipolar and bipolar, plasma scalpels, ultrasonic scalpels and cryogenic scalpels. In addition, microwave energy has been used for specific applications in treating tumors and coagulating muscle tissue.

The application of a high power microwave field in surgery involving highly vascular tissue appeared in an article entitled "A New Operative Procedure Of Heptatic Surgery Using A Microwave Tissue Coagulator" (Arch Jan Chir 48 (2), page 160–172, Marz 1979) authored by Katsuyoshi Tabuse. Tabuse described heptatic resection performed in rabbits, using a simple "burning needle" device which was obtained by open circuiting a coaxial line and extending the inner conductor as a needle a few centimeters. Resection was obtained by a series of punctures each accompanied by the application of microwave power. This technique involved a number of limitations. The antenna permitted coagulation for a small radial distance around the needle to a puncture depth of approximately 10 mm. Resections were obtained by series of coagulating punctures of the tissue followed by scalpel trans-section through the coagulated area. The resulting procedure was time consuming and impractical for coagulating the large surfaces to be anticipated in a human liver or spleen resection.

The use of microwave energy to coagulate muscular tissue is also disclosed in U.S. Pat. No. 4,315,510 which issued to Kihn on Feb. 16, 1982. This patent discloses a "Method Of Performing Male Sterilization" by coagulating the muscle tissue portions of an anatomical element.

The first commercial radio frequency scalpels appeared in 1926, but were not generally accepted by surgeons until the development of non-explosive anesthetics in the late 1950's. With the development of solid state units in the 1970's, they have been widely installed in operating rooms. Generators supply power in the range of 40 to 400 watts at frequencies between 2.5 and 27 $MH_z$. Cutting and coagulation occur at the tip of a probe electrode, where the current is concentrated. The current then spreads through the body to a large "butt" plate upon which the patient rests. The cutting and coagulation are determined by the power and wave form. A sinusoid wave produces cutting, a dampened sinusoid wave produces coagulation with little cutting. Interrupted sinusoids produce a variable degree of cutting and coagulation. The reasons for these variations are not well understood. A number of hazards are still associated with the use of the radio frequency scalpel. Although non-explosive anesthetics are used, there is still the danger of explosions of body gases, the currents can interfere with pacemakers, and radiation disrupts electronic monitors.

Examples of such scalpels are disclosed in U.S. Pat. Nos. 3,089,496 and 4,318,409. The primary difference between the present invention and conventional radio frequency surgical scalpels is the mechanism by which coagulation is achieved. In conventional electrosurgery, the cutting of tissue is achieved by an electric current discharge. The region of intense current is short in length but heats the tissue intensely causing the cells to actually burst into steam. Therefore, the cutting is caused by the discharge from an appropriate electrode to the tissue. Cutting is not achieved by the sharpened edge of a metallic blade. Desiccation (cautery) in conventional electrosurgery is caused by holding the active electrode in firm contact with the tissue, the electric current passing directly into the tissue, thereby causing localized $I^2R$ (ohmic) heating. Because the $I^2R$ heating occurs at the point of contact between the active electrode and the tissue, the cautery or coagulation effect is very shallow, too shallow to be effectively used to cauterize highly vascular tissue areas such as spleens or livers.

In the present invention, coagulation is achieved by microwave energy that is dissipated into the tissue being severed. The physical mechanism of the microwave heating effect is the absorption of energy by the excitation of rotational motion of the polar water molecules, rather than by ohmic heating due to ionic currents. Thus, the microwave coagulating scalpel does not require that the patient be grounded through a buttplate or other arrangement as is required by conventional radio frequency scalpels.

U.S. Pat. Nos. 3,987,795 and 4,196,734 disclose combination systems and employ both ohmic heating elements and radio frequency elements in a surgeons scalpel.

U.S. Pat. No. 3,826,263 and U.S. Pat. No. 29,088 disclose the use of resistance heating elements in a scalpel.

U.S. Pat. No. 3,786,814 discloses a cryogenic scalpel. This reference also discloses the use of Paralene, Kel-F, Teflon, Silicones and Lubrichrome to prevent the adhesion of tissue to the scalpel.

U.S. Pat. No. 4,273,127 discloses the use of a laser for cutting and coagulating tissue. A carbon dioxide (10.6 $\mu$m) laser scalpel does produce coagulation, but blood loss is still excessive in incisions involving large areas of highly vascularized tissue. Laser photo-coagulating scalpels have also been successfully tested for skin excisions using an argon laser (0.5 $\mu$m), and it was suggested that a Nd:YAG at 1.06 μm, would provide penetration sufficient for coagulation of vascular organs but subsequent tests have caused excessive tissue damage. However, the relative advantages of the microwave device include the use of lower, more penetrating frequencies to obtain coagulation in depth, simplicity of design, and widespread availability of small, compact microwave diathermy units which can serve as the power source for a microwave coagulating scalpel.

U.S. Pat. No. 3,903,891 discloses a method and apparatus for generating plasma for use in a coagulating scalpel. Again, the method and means for generating the microwave energy is substantially simpler than the apparatus required to create and maintain a plasma field.

U.S. Pat. No. 3,636,943 discloses a method and apparatus for using ultrasonic energy to close off small severed blood vessels in surgery. The function of an ultrasonic device is substantially different than the function of a microwave coagulating device. The ultrasonic device produces heat by means of mechanical friction whereas the microwave coagulating device produces heat by molecular rotation.

SUMMARY OF THE INVENTION

The present invention is a surgical instrument for simultaneously cutting and coagulating vascular tissue. The instrument is a microwave coagulating scalpel wherein the scalpel blade includes both a microwave radiator for emitting microwave radiations in the immediate proximity of the blade, and a surgical cutting edge for severing highly vascular tissue. The instrument also includes means for generating microwave energy having a frequency of 100 $MH_z$ to 13,000 $MH_z$. The scalpel also includes means for manipulating the cutting edge to enable the surgeon to obtain tactile feedback therefrom. An insulated and flexible conductor is provided to transmit the microwave energy from the microwave generator to the scalpel blade.

In addition to the scalpel, circuitry is provided in the microwave generating means for measuring the reflected microwave energy that returns along the microwave conductor. The microwave radiator loop diameter is related to the microwave wave length to provide a high degree of matching impedance when the energy is transmitted into highly vascular tissue. When the blade or cutting edge is removed from the tissue, the microwave radiation is propogated through air, and a substantial mismatch thereby results between the loop and the wave propagating through air. This mismatch results in reflected microwave energy being returned to the microwave generating means. A bolometer or other equivalent device for sensing reflected microwave energy is provided to de-energize the microwave source when the reflected microwave energy exceeds a predetermined level. A manual switch means is provided to enable the surgeon to re-establish the microwave energy as the cutting edge engages the highly vascular tissue. Additionally, choke means may be provided between the blade and the handle to prevent microwave energy from traveling along the exterior surface of the handle to the surgeons fingers. A Teflon or other highly non-wetted surface is provided to prevent adhesion of the tissue or coagulated blood to the edge of the microwave radiator. Alternatively, ultrasonic energy may be employed to prevent adhesion.

The microwave coagulating scalpel is particularly useful in highly vascular organs such as the spleen or liver. By varying either the power or the frequency applied to the microwave radiator or the speed of cutting, the depth of tissue coagulation can be controlled.

It is therefor the object of the present invention to provide a microwave coagulating scalpel that can be successfully used in splenic and heptatic surgery involving the simultaneous severing and coagulation of highly vascular tissue or in the repair of damaged organs where bleeding is occurring.

It is another object of the present invention to provide a simple low cost and inexpensive means for heptatic and splenic surgery that does not require a high degree of technical skill to accomplish.

It is another object of the present invention to utilize presently existing and relatively inexpensive microwave generating means to generate microwave energy for a microwave coagulating scalpel to be used on highly vascular tissue.

It is another object of the present invention to provide a safety feature for a microwave coagulating scalpel, that correlates the microwave radiator to the wave length of the microwave energy, when the energy is propogated through highly vascular tissue. When the microwave radiator is removed from the highly vascular tissue, the radiator is highly mismatched in the air. This provides an inherent safety feature to reduce radiation from the microwave radiator when the scalpel is withdrawn from the patient.

DETAILED DESCRIPTION OF THE DRAWINGS

FIG. 1 is a side view of an experimental model of a microwave coagulating scalpel.

FIG. 2 is an enlarged cross-sectional view of the microwave radiator shown in FIG. 1, illustrating the pattern of microwave radiation.

FIG. 3 is an end view of the scalpel illustrated in FIG. 2.

DETAILED DESCRIPTION OF THE PREFERRED EMBODIMENTS

Figure 7:
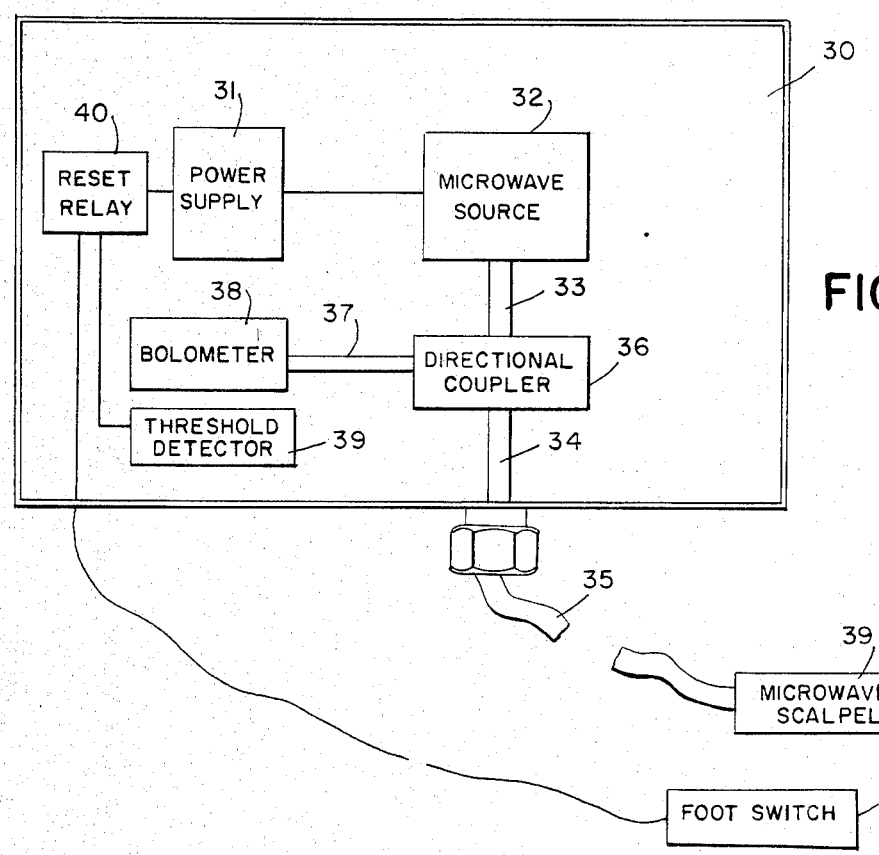
FIG. 7 is a block diagram of a microwave generating means constructed in accordance with the present invention.

A microwave coagulating scalpel constructed in accordance with the present invention was constructed as illustrated in FIG. 1. As illustrated, a conventional surgical blade 11 was soldered to the internal conductor 12 and the outer or external conductor 13 of a rigid coaxial conductor 10. The rigid coaxial conductor included a solid Teflon core 14 which extended from the end of the coaxial member to the coaxial coupling means 15. A locking key 16 was used to lock an insulated handle member 17 to the outer conductor 13 of the rigid coaxial line. The coaxial connector 15 was connected to a standard 2450 $MH_z$ microwave generator by means of a low loss flexible coaxial conductor as illustrated in FIG. 7. A surgical blade 11 illustrated in FIG. 1 formed a radiating loop 18 between the inner conductor 12 and the outer conductor 13. The blade surface 19, except for the cutting edge 20, is covered with a Teflon film to prevent tissue from adhering to the surface of the blade during the cutting and coagulating operation.

As illustrated in FIG. 2, the standard surgical blade 11 is soldered at the joint indicated by 12a, and along the edge 13a and 13b to provide for efficient transmission of microwave energy from the coaxial conductor to the blade. As illustrated in FIGS. 2 and 3, the microwave scalpel has been equipped with a hand switch 21 which can be used by the surgeon to re-energize the power source during surgery.

In the preferred embodiment of the invention, means are provided for measuring the reflected microwave energy when an impedance mismatch results between the microwave radiating loop 18 and the medium to which the microwave energy is transmitted. When the mismatch is detected, the microwave source is de-energized. When the surgeon desires to re-establish the microwave energy field, the microwave source is energized by means of a hand switch 21, or a foot switch 22, as illustrated in FIG. 7.

The scalpel blade and its microwave radiator are more fully illustrated in FIG. 2. A microwave radiator comprises a radiator loop 18 formed between the blade 11 the inner conductor 12 and the outer conductor 13 of the rigid coaxial conductor 10. When immersed in vascular tissue the small loop is electrically well matched (input VSWR ~ 1.6) since the loop diameter is of the same order of magnitude as the wave length at 2450 $MH_z$ in tissue and/or blood. The small loop is highly mismatched in air (input VSWR ~ 100), an inherent safety feature which acts to prevent radiation when the scalpel is withdrawn from the highly vascular tissue. This mismatch implies that less than 0.04 percent of the input power is radiated when the blade is in air, while 86 percent of the power is radiated when immersed in highly vascular tissue. In each case, the balance of the power is reflected back into the coaxial cable, and thus back to the generator. Loss in the feed cable is approximately 7 percent in each direction. A low loss transmission line parameter is required since successful operation of the microwave scalpel has been found to require power of approximately 100 watts. This high power level must be transmitted from the generator to the scalpel without excessive heating due to ohmic losses in the flexible cable that connects the generator and the coaxial wave guide feed to the blade.

The heating pattern 23 of the microwave field of the loop has been seen to be nearly circular in the plane of the blade, centered approximately mid-way between the loop center 25 and the point of the blade. The loop center is measured along the diameter A—A' as illustrated in FIG. 2. The depth of penetration of a 2450 $MH_z$ heating field into a highly vascular tissue is approximately 8 mm. for the configuration illustrated in FIG. 1. FIG. 2 is approximately twice the size of the test scalpel illustrated in FIG. 1.

The 8 mm. penetration depth is the depth at which the power of a plane wave at this frequency would decay to $e^{-1}$ (=37%) of its initial value. In the near field of the loop, the wave is much more intense. After the first millimeter or two, the wave front decays as a function of distance to the $\gamma^{-3}$ power with a slower expontential decay realized after the first centimeter of penetration. The physical mechanism of the microwave heating effect is the absorption of energy by excitation of rotational motion of the polar water molecule, rather than by ohmic heating due to ionic currents.

As illustrated in FIGS. 1–3, the surgical blade 11 is coated with a Teflon (tetrafluoroethylene resin) coating 19 which covers all of the blade except cutting edge 20. The Teflon coating prevents the adherence of tissue and coagulated blood on the scalpel blade during the surgical procedure. While the loop 18 has been illustrated in FIGS. 1–3 for the purposes of clarity of illustration, it has been found expedient to cover the loop with Teflon film.

The means for generating microwave energy is illustrated in FIG. 7. As illustrated, a microwave generator 30 includes a power source 31, a microwave source 32, and a wave guide means 33, 34 for coupling the output of the microwave source to a flexible coaxial cable 35.

The flexible coaxial cable 35 may be any type of wave guide, but in the preferred embodiment is comprises of a flexible inner conductor, a foamed and flexible Teflon core, a copper tape outer conductor, and a vinyl rubber outer insulator. Such a cable is manufactured and sold under the trade name of "Gore-Tex" ® available from W. L. Gore and Associates, Inc. 551 Papermill Road, Newark, Del., 19711.

As illustrated in FIG. 7, the means for generating microwave energy also includes a directional coupler 36 with a third wave guide 37. The third wave guide 37 is connected to a bolometer 38 or some other means for measuring reflected microwave energy returned from the microwave scalpel 39 illustrated in FIG. 7. Reflected microwave energy results from the previously described impedance mismatch when the microwave loop is withdrawn from the highly vascular tissue. The output of the bolometer is connected to a threshold detector 39 which is in turn connected to a reset relay means 40. When the output of the bolometer or other means for measuring reflected microwave energy exceeds a predetermined level, the threshold detector disengages the power source 31 by means of the reset relay 40. When the surgeon is again ready to coagulate or sever the highly vascular tissue, the relay is reset by means of foot switch 22. Alternately, as illustrated in FIGS. 2 and 3, the reset relay means 40 may be activated by means of a hand switch 21.

The microwave source 32 is conventionally a magnetron having an effective power output of 100 watts. Alternately, it can be a klystron tube with a traveling wave tube amplifier to provide the necessary power, or other microwave generator.

The operating frequency of the device is broadly defined as 100 $MH_z$ to 13,000 $MH_z$ and may use conventional diathermy generators available commercially at 915 $MH_z$, 2450 $MH_z$, or 5800 $MH_z$. The distinction between microwave energy and radio frequency energy derives from the fact that in tissue, absorption of electromagnetic energy in the microwave range is due to polarization current. At low frequencies, such as radio frequency, the body acts as a conductor and the electric field is shunted by conduction current. At higher frequencies, the penetration depth rapidly becomes much smaller. Only in the microwave range is penetration significant. As indicated previously, the loop diameter of the microwave radiator is sized to provide resonance in highly vascular tissue. In the near field of a small loop antenna, the power deposition pattern is a function of $(r/\lambda)$ and $(a/r)$ where r is distance from the loop, a is the loop radius and $\lambda$ is the wave-length. While 100 $MH_z$ to 13,000 $MH_z$ has been broadly defined as the microwave operating range, it should be pointed out that the frequency that is selected may be varied to vary the penetration of the microwave field in the vascular tissue. The depth of penetration for the microwave energy field is inversely proportional to frequency. This means the depth of coagulation may be regulated by selecting the appropriate microwave energy frequency, and loop radiator diameter 25. Thus, it may be desireable to provide a plurality of microwave sources 32 within the microwave generating means 30 to enable the surgeon to select the depth of penetration desired for the coagulating field.

Because the microwave energy is absorbed in the tissue when the blade is immersed in the tissue, and reflected back into the microwave generating means when the blade is removed, it is calculated that less than 5 watts are radiated into the air at any given time. To test the levels of stray microwave radiation, a Narda 8316 non-ionizing radiation monitor and a model 8321 probe were used as a monitor during one surgical experiment. The radiation level was seen to remain far below the ANSI safety standard of $\frac{1}{2}$ milliwatt per centimeter$^2$ at all distances exceeding about 7 inches from the blade tip. Consequently, at the highest levels, only a small fraction of the milliwatt per centimeter$^2$ would be present at normal distances to the surgeons eyes. This means that both the power density level and the exposure times would be at least 2-3 orders of magnitude below the levels required for microwave cataractogenesis.

Figure 5:
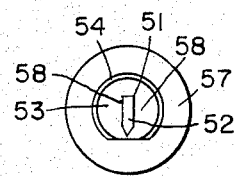
FIG. 5 is an end view of the scalpel illustrated in FIG. 4.
Figure 4:
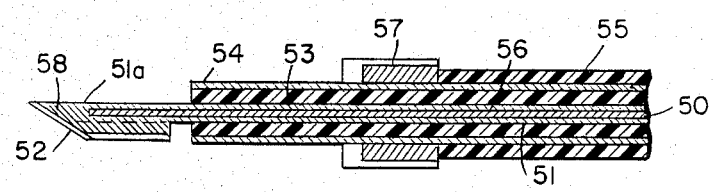
FIG. 4 is a side and partially cross-sectioned view of a scalpel constructed in accordance with the teachings of the present invention.
Figure 6:
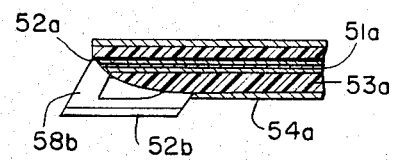
FIG. 6 is a partial cross-sectional view of a perferred embodiment of the present invention.

A preferred embodiment of the invention is illustrated in FIGS. 4–6. In this embodiment, the scalpel assembly is formed of a microwave conductor having an laminated structure. An inner copper conductor 50 is laminated within a surgical steel conductor 51 which is enlarged at its terminal end 51a to form a surgical cutting edge 52 for the surgeon. A rigid Teflon core 53 separates the inner conductor from the outer coaxial wave guide conductor 54 and the insulated handle member 55. It should be noted that the handle member 55 extends from the coaxial coupler 56 to a microwave choke 57 which is formed between the blade member 52 and the handle member 55. The purpose of the choke 57 is to prevent any surface waves which may exist on the outer surface of conductor 54 from traveling backwards along the outer surface of the conductor to the surgeons fingers. The microwave coupler 56 connects the conductor 35 to the microwave generating means 30.

FIG. 4 illustrates a unipolar microwave scalpel having a cutting edge 52 and a microwave generating field that exists between the blade member 52 and the outer conductor 54. FIG. 6 illustrates a loop scalpel formed of the laminated construction illustrated in FIG. 4. An inner copper conductor 51a is sandwiched between two layers of surgical steel 52a that define a cutting edge 52b. The outer portion of the loop is integrally connected to the outer coaxial shield 54a and separated therefrom by means of the rigid Teflon core 53a. As illustrated in FIGS. 4–6, the scalpel is intended to be a disposable scalpel which may be discarded after each operation. The flexible conductor 35 may be sterilized and reused between each use. As indicated previously, with respect to FIGS. 1–3, the outer surface of the scalpel blade 52 is covered with a Teflon layer 58, 58b to prevent the adhesion of coagulated blood and tissue to the scalpel blade. Only the cutting edge 52, 52b remains uncovered.

EXPERIMENTAL TRIALS

Ten mongrel dogs weighing approximately 20 kg. were given general anesthesia using nembutal. After routine povidone iodine preparation and draping, a midline incision was made. The canine spleen was mobilized, and gastrosplenic ligamentous attachments were cleared off the spleen at the proposed point of resection. The major segmental branches of the splenic artery were not ligated, however, and no clamps were used on the splenic pedicle. The spleen at either the superior or inferior pole was subjected to a sharp surgical trauma. Using the microwave coagulating scalpel at 100 watts, partial splenectomies were done, resecting the injured half of the spleen. The amputations required only 5–10 minutes, and the cut surfaces were dry and free of seepage at the end of this period. In other animals, areas with linear and/or stellate lacerations were directly coagulated without splenectomy. Suture ligatures were used only to ligate large vessels in the hilar region. The omentum was removed in four of the dogs to assess its role in subsequent healing. At the time of initial surgery, the resected portions of the spleens were sectioned for histologic studies. The spleens were also photographed before and after the splenorrhapies. Four of the dogs spleens were assessed post-operatively for function by liver spleen scans. Technetium$^{99m}$ sulfur colloid was injected intraveneously at a dose of 2 millicuries. Imaging of spleens was performed approximately 10 minutes after injection. Scans were obtained on dogs 2, 3, 4, and 5 at 2 weeks postoperatively. The dogs were sacrificed at 2, 3, 7, and 8 weeks, at which time all spleens were again photographed and sectioned for histologic studies. Hemotoxylin and eosin staining was used for all histologic slides.

By gross inspection all spleens appeared normal. Adherences of omentum to the coagulated surface of the spleen was observed in all cases where omentectomy was not performed. When omentectomy had been carried out, the coagulated surface was found to be adherent to the small bowel or to other peritoneal surface in all cases. There were no hematomas, intra-abdominal abscesses, splenic necroses or splenic abscesses in any of the animals. Technetium scans demonstrated functional splenic tissue two weeks after operation in the four dogs studied. Histologic assessment at the initial procedure revealed an area of coagulation necrosis which varied in depth from 3 mm to 10 mm. This variation in depth of injury was due to variations and exposure time to the microwave scalpel. The scalpel blade used for the first five dogs was not teflon coated, and adherence of coagulated tissues to the blade slowed these transactions to produce a greater depth of coagulation. In the last five dogs, where teflon-coated blades were used, the average depth of injury was only 4 mm. Histologically, the region of necrosis progressed from an area of complete accellularity at the surface, through a region continaing hemorrhagic thrombosis associated with infiltration of lymphocytes and leukocytes, and then a sharp transition to normal spleen. Spleens observed two weeks following injury demonstrated a zone of demarcation between the normal spleen and the acellular area. This zone contained increased numbers of hemosiderin-laden macrophages and firoblasts. At three weeks, the zone became more organized into a fibrous pseudocapsule, with evidence of neovascularization. At seven and eight weeks, this pseudocapsule was well developed, and the outer acellular area was largely reabsorbed. The depth of the acellular area was in rough agreement with the temperature increase observed in the spleen adjacent to the cut surface. This increase was monitored with a thermocouple during one trial. The temperature increase at one centimeter from the coagulated edge was 9° C. at two centimeters 2° C. and at three centimeters 1° C. Blood loss and hemostatic time were measured in an additonal six dogs to compare standard mattress-suture and microwave scalpel techniques. The splenic poles and sequence of techniques were alternated. With standard mattress-suture techniques, the mean blood loss was 45 ml. and the hemostatic time was 20–30 minutes. With the microwave scalpel technique the blood loss was 5 ml and the hemostatic time was 5–10 minutes.

I claim:

1. A surgical instrument for simultaneously cutting and coagulating tissue, said instrument comprising:
   (a) means for generating microwave energy having a frequency selected from the range of 100 MHz to 13,000 MHz;
   (b) a scalpel blade having a cutting edge for severing tissue, said blade also having a microwave radiator means therein for emitting microwave radiations in the proximity of said cutting edge;
   (c) means for manipulating said scalpel blade which includes an insulating means to enable a surgeon to manipulate the cutting edge and obtain tactile feedback therefrom;
   (d) insulated conductor means for transmitting said microwave energy to said microwave radiator means.

2. A surgical instrument as claimed in claim 1, wherein said means for generating microwave energy includes a means for measuring reflected microwave energy, and directional coupling means for connecting said generating means with said conductor means.

3. A surgical instrument as claimed in claim 2, wherein said generating means further includes a threshold detector means for de-energizing said generating means for generating microwave energy when said reflected energy exceeds a predetermined level.

4. A surgical instrument as claimed in claim 3, which further includes a power source coupled to said means for generating microwave energy, said power source being de-energized by said threshold detector means when said reflected microwave energy exceeds a predetermined level.

5. A surgical instrument as claimed in claim 1, or 2 or 3 which further includes a remote manual switch means to enable the surgeon to energize said microwave generating means as said cutting edge engages said tissue.

6. A surgical instrument as claimed in claims 1 or 2 or 4, wherein said blade and manipulating means is detachable and disposable.

7. A surgical instrument as claimed in claims 1 or 2 or 4 which said microwave radiator means is formed of a loop of conductive metal, said loop having a diameter on the same order of magnitude as the wavelength of said microwave energy, when said energy is propagated through tissue.

8. A surgical instrument as claimed in claims 1 or 2 or 4 wherein said microwave generating means generates microwave energy at 2450 MHz.

9. A surgical instrument as claimed in claims 1 or 2 or 4 wherein said microwave generating means generates microwave energy at 5800 MHz.

10. A surgical instrument as claimed in claims 1 or 2 or 4 which further includes a microwave choke means to prevent surface waves from traveling along the manipulating means.

11. A surgical instrument as claimed in claims 1 or 2 or 4 wherein said microwave energy generating means generates microwave energy at 915 MHz.

12. A surgical instrument for cutting and coagulating tissue, said instrument comprising:
    (a) a microwave generator for generating microwave energy having a frequency between 400 MHz and 13,000 MHz;
    (b) a microwave radiator means having an integral surgical cutting edge for severing tissue, said radiator means providing a loop radiator for said energy, said loop having a diameter on the same order of magnitude as the wavelength of said microwave energy, when said energy is propogated through tissue;
    (c) conductor means for transmitting said microwave energy from said microwave generator to said microwave radiator means;
    (d) means for manipulating said cutting edge and energizing said microwave generator when said cutting edge engages said tissue.

13. A surgical instrument as claimed in claim 12 wherein said microwave generator includes:
    (a) means for measuring microwave energy reflected back along said conductor means;
    (b) a threshold detector means for detecting when said reflected energy has exceeded a predetermined level and;
    (c) means for de-energizing said microwave generator when said threshold detector means detects that said reflected energy has exceeded said predetermined level.

14. A surgical instrument as claimed in claims 12 or 13 wherein said microwave radiator means is detachable and disposable from said microwave generator.

15. A surgical instrument as claimed in claims 12 or 13 wherein said microwave generator generates microwave energy at 2450 MHz.

16. A surgical instrument as claimed in claims 12 or 13 wherein microwave generator generates microwave energy at 5800 MHz.

17. A surgical instrument as claimed in claims 12 or 13 wherein said means for manipulating said cutting edge comprises a rigid coaxial conductor having an insulated handle member surrounding said rigid coaxial conductor.

18. A surgical instrument as claimed in claim 17 which further includes a microwave choke mounted between said microwave radiator means and said handle member.

19. A surgical instrument for radiating microwave energy to coagulate tissue severed during surgery, said instrument comprising:
    (a) a scalpel blade assembly for microwave surgery, said blade assembly having;
       (i) a microwave radiator mounted within said blade assembly, said radiator radiating a near field of microwave radiation when coupled to a source of microwave energy;
       (ii) a surgical cutting edge for severing tissue during surgery, said cutting edge traversing the near field of microwave radiation created by said microwave radiator;
    (b) a handle means for supporting said blade assembly during surgery;
    (c) coupling means for receiving microwave energy having a frequency selected from the range of 400

MH$_z$ to 13,000 MH$_z$ and supplying said energy to said radiator.

20. A surgical instrument as claimed in claim 19 which further includes:
(a) a means for generating microwave energy having a frequency selected from the range of 400 MH$_z$ to 13,000 MH$_z$;
(b) a switch means for enabling a surgeon to selectively energize the microwave radiator with microwave energy during surgery;
(c) conductor means for conducting microwave energy between said means for generating microwave energy and said coupling means.

21. A surgical instrument as claimed in claim 1 or 20 wherein said means for generating microwave energy will selectively generate energy at more than one frequency to enable the surgeon to select the frequency to be utilized for a specific surgical procedure.

22. A surgical instrument as claimed in claim 19 or 20 wherein the microwave radiator is a loop radiator having a diameter on the same order of magnitude as the wavelength of the microwave energy to be supplied to the radiator.

23. A surgical instrument as claimed in claim 19 or 20 wherein said blade assembly is disposable.

24. A disposable microwave scalpel for use with a means for generating microwave energy in the frequency range of 100 MH$_z$ to 13,000 MH$_z$ said disposable scalpel comprising:
(a) a scalpel blade, said blade having;
(i) a surgical cutting edge for severing tissue;
(ii) a microwave radiator in the proximity of the cutting edge for coagulating fluids in the tissue severed by said cutting edge;
(b) an insulated handle means for manipulating said edge and said radiator to enable the surgeon to manipulate the cutting edge and obtain tactile feedback therefrom;
(c) a means for coupling said radiator to a source of microwave energy.

25. A disposable scalpel as claimed in claim 24 wherein said microwave radiator is a loop radiator mounted within the scalpel blade.

26. A disposable scalpel as claimed in claim 25 wherein said loop radiator defines a near field of microwave radiation when coupled to a source of microwave energy; and said blade has said cutting edge crossing said near field.

27. A disposable scalpel as claimed in claim 24 or 25 or 26 which further includes a choke means to prevent the propagation of surface waves along said handle means.

28. A disposable scalpel as claimed in claim 24 or 25 or 26 which further includes a remote manual switch means to enable a surgeon to energize the source of microwave energy as said cutting edge energizes said tissue.

29. A disposable scalpel as claimed in claim 25 or 26 which said loop radiator has a diameter on the same order of magnitude as the wave length of the microwave energy to be supplied to the radiator.

30. A disposable scalpel as claimed in claim 24 or 25 or 26 in which said insulated handle means further comprises a coaxial microwave conductor between said means for coupling and said microwave radiator.

31. A method for simultaneously cutting and/or coagulating tissue, said method comprising:
(a) generating microwave energy having a frequency of 100 MH$_z$ to 13,000 MH$_z$;
(b) conducting said microwave energy through a conductor to a microwave radiator formed within a scalpel blade to propogate microwave energy;
(c) simultaneously:
(i) severing said tissue with a surgical cutting edge formed on said scalpel blade while;
(ii) radiating microwave energy from said radiator to cauterize the severed tissue and coagulate vascular fluids contained therein,
(d) removing said microwave radiator after said tissue has been cut and said fluids coagulated.

32. A method for simultaneously cutting and coagulating tissue as claimed in claim 31 which further includes the steps of:
(a) forming said cutting edge along one edge of a loop radiator;
(b) matching the diameter of the loop to the wave length of the microwave energy, when said energy is propogated through highly vascular tissue.

33. A method for simultaneously cutting and/or coagulating tissue as claimed in claim 31 or 32 which further includes the steps of:
(a) measuring the microwave energy reflected back from said microwave radiator along said conductor;
(b) terminating said microwave energy when the reflected energy exceeds a predetermined level.

34. A method for simultaneously cutting and coagulating tissue as claimed in claim 31 or 32 which further includes the step of manipulating the cutting edge with said conductor to enable a surgeon to obtain tactile feedback therefrom.

35. A method for simultaneously cutting and coagulating tissue as claimed in claim 24 which further includes the step of choking external energy waves that may propogate along the external surface of the conductor from said radiator.

36. A method for simultaneously cutting and coagulating tissue as claimed in claims 31 or 32 wherein said microwave energy is generated at 2450 MH$_z$.

37. A method for simultaneously cutting and coagulating tissue as claimed in claims 31 or 32 wherein said microwave energy is generated at 5800 MH$_z$.

38. A method for simultaneously cutting and coagulating tissue as claimed in claim 31 or 32 which further includes the step of varying the frequency of the microwave energy to vary the depth of coagulation.

39. A method for simultaneously cutting and coagulating highly vascular tissue as claimed in claim 31 or 32 which further includes the step of generating 20 to 300 watts of microwave energy for transmission to said radiator.

40. A method for simultaneously cutting and coagulating tissue as claimed in claim 31 or 32 which further includes the step of energizing a microwave generator with a remote location switch to enable a surgeon to generate said microwave energy as the surgical cutting edge severs said tissue.

* * * * *